United States Patent [19]

Ferrara

[11] 4,083,788
[45] Apr. 11, 1978

[54] BLOOD SERUM-ISOLATION DEVICE

[76] Inventor: Louis T. Ferrara, 2988 Avenue "T", Brooklyn, N.Y. 11229

[21] Appl. No.: 633,399

[22] Filed: Nov. 19, 1975

[51] Int. Cl.$^2$ .......................................... B01D 21/26
[52] U.S. Cl. ........................... 210/516; 210/DIG. 23; 23/259; 128/2 F; 128/2 G
[58] Field of Search ................. 23/259, 292; 210/DIG. 23, DIG. 24, 516; 128/2 F, 2 G; 233/1 A, 26

[56] References Cited

U.S. PATENT DOCUMENTS

| | | | |
|---|---|---|---|
| 3,508,653 | 4/1970 | Coleman | 210/DIG. 24 |
| 3,832,141 | 8/1974 | Haldopoulos | 23/259 |
| 3,894,952 | 7/1975 | Ayres | 210/DIG. 23 |
| 3,929,646 | 12/1975 | Adler | 210/DIG. 23 |
| 3,957,654 | 5/1976 | Ayres | 210/DIG. 23 |

*Primary Examiner*—Sidney Marantz

[57] ABSTRACT

A blood serum separation unit which includes a tubular structure having openings at each of opposite ends and having a slidable disk element mounted within a base end thereof, having an outside diameter substantially less than an inside diameter of the tubular element such that upon centrifugal action the slidable disk will be slidable therewithin by torque of centrifugal action, and the tubular element being mounted substantially flushly within but removable from an outer tube having an upper open end and having a stopper-plug which when inserted plugs both the outer tubular container and the tubular element located therewithin, the plug being of a composition penetrable by a tubular needle for introducing blood from a subject to space within the tubular container and tubular element, the disk being of a specific gravity intermediate between those specific gravities of blood serum and blood coagulant precipitate whereby upon inversion of the blood-containing tube and the thereafter subjection of the same to centrifugal action forces, the coagulant precipitate is separated and compacted at an upper end of the tubular element by the disk and upon removal of the stopper-plug serum is left isolated in the remaining outer tube base, the coagulant precipitate having been removed with the inner tubular element.

2 Claims, 7 Drawing Figures

U.S. Patent      April 11, 1978      4,083,788
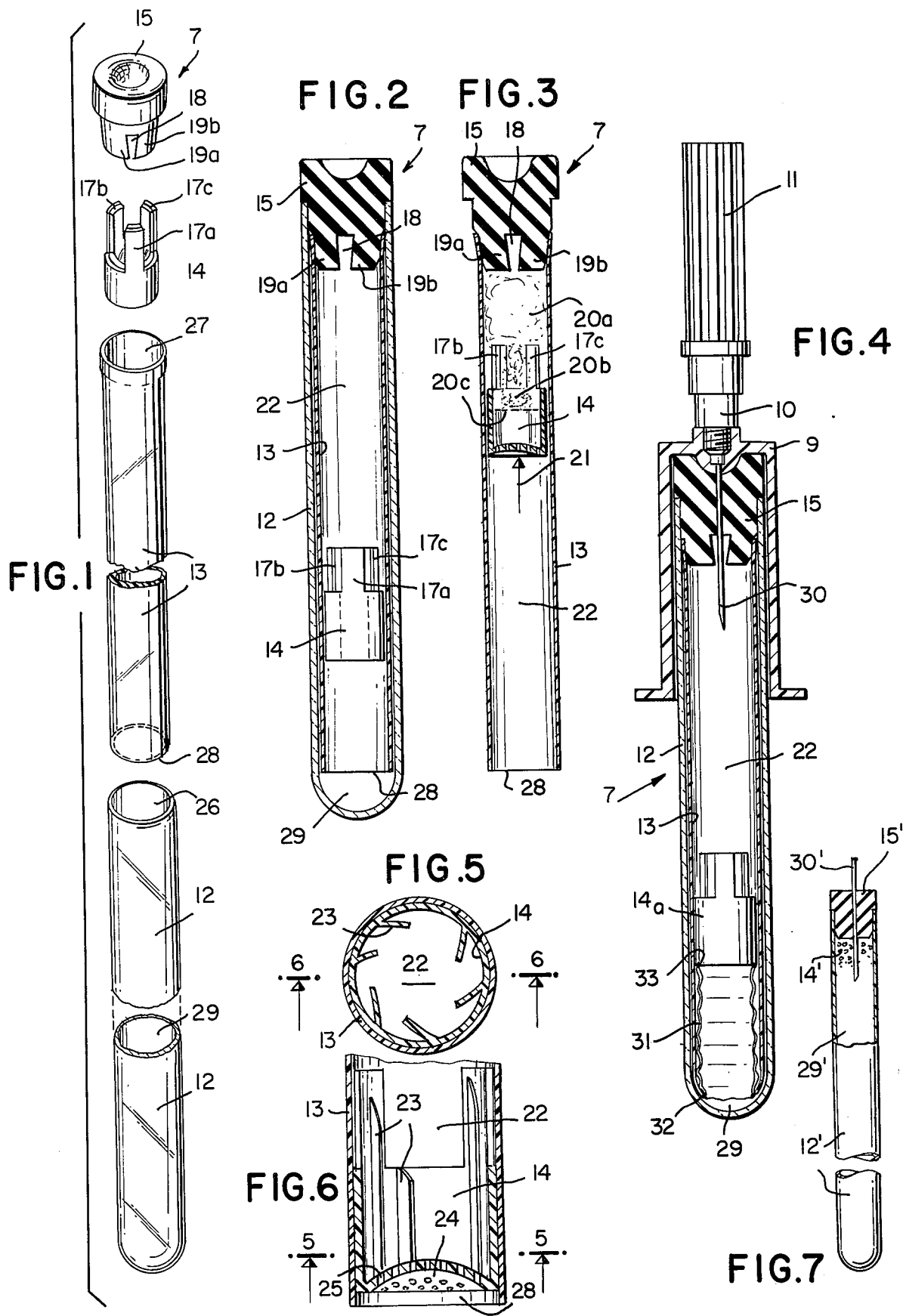

BLOOD SERUM-ISOLATION DEVICE

This invention relates to an improved mechanism and device for facilitating separation of blood serum from blood sample.

BACKGROUND TO THE INVENTION

Prior to the present invention, it has been a common practice to withdraw blood from a patient through a tubular needle into an evacuated test tube or specimen tube, after which the tube with the blood sample contained therein, still sealed with the stopper-plug, after withdrawal of the needle from the stopper-plug, is placed into a centrifuge and subjected to centrifugal action forces by which blood serum becomes separated from solid coagulant precipitate-contents of the blood, which content(solids) are by the centrifugal action centrifuged into a lower base portion of the tube, the serum being in the upper portion of the tube as a result of the serum being of a lower specific gravity. Thereafter, the normal practice would be to pour the serum carefully into a second tube carefully in order to avoid disturbance of the blood solids in the bottom of the centrifuged tube, after which the separated serum in the second tube is subjected to the predetermined analytic precedures. Such a procedure of separation of the serum from the centrifuged blood coagulant precipitate as described above is extremely time consuming, when conducted as described above typically. Such prior procedure also requires a significantly large degree of skill in order to handle the second tube into which the serum is decanted. Even though the greatest of care may be exercised by a skilled technician, there is always a real possibility that the loose blood-solids coagulant precipitate resting within the base of the tube will become disturbed with a resulting of a portion of such cells and other precipitate matter into the second tube with the decanting into the second tube. Alternatively, in care not to pour solids from the centrifuged tube into the second tube, the tendency is to leave a portion of the serum within the centrifuged tube, thereby reducing volume of serum collected in the second tube. As inferred above, in the absence of skill and experience, a technician may readily drop, spill, or otherwise mar the useable nature of the serum, difficulty being compounded by the simultaneous handling of the two tubes while trying to carefully decant from one to the other. Without excessive skill and experience, not only are the above problems compounded, but additionally a real possibility of absurd or unrealistic time of performance exists, rendering heretofore methods and equipment totally unsatisfactory and unrealistic and, by the present invention, the prior methods and equipment becoming totally obsolete, in relation to realistically the many duties and lack of adequate time of the typical overworked technician, as well as the need for speed in the performance of such analytical procedures often involving life and death situations dependant upon speed of diagnosis based on tests utilizing the above-noted procedures and equipment, if not at least a severe illness in need of prompt diagnosis.

SUMMARY OF THE INVENTION

Accordingly, objects of the present invention include overcoming one or more difficulties and problems and disadvantages of prior procedures and devices for the separation of blood serum from a blood sample.

Another object is to obtain a novel device having novel advantages and subject to the employement of novel and advantageous procedures also contributing to the overcoming of problems and disadvantages of the types cited above.

Another object is to obtain a novel procedure for the ready-isolation and separation of blood serum and centrifugable blood solids with a minimal degree of skill and time required to effect such procedures.

Other objects become apparent from the preceding and following disclosure.

One or more objects are obtained by the invention as defined herein.

Broadly the invention may be defined as a novel blood serum separation device including a specimen container preferably of elongated tubular shape open at at-least one end thereof, and having mounted therein a material of a specific gravity intermediate between that of blood serum and blood solids subject to normal centrifugal forces of analytical laboratory centrifuging equipments, and being subject to movement within space of the enclosing tube, such that upon introduction of the blood sample specimen into the tube space and thereafter subjecting the tube and its contents to centrifugal action forces, the blood serum becomes separated and isolated from blood solids coagulant precipitant by the intermediate specific gravity-material(s) being located therebetween and pressed against the coagulant precipitate as a result of the intermediate specific gravity mass being concurrently subjected to the centrifugal action during the centrifuging operation. By virtue of the intermediate specific-gravity material being of a property as to not readily disintegrate and as to thereby hold-in-place the coagulant precipitate as a plug, the blood serum may be easily poured from the top of the tube without significant risk of pouring concurrently therewith any of the cells or other parts of the coagulant precipitate while easily decanting substantially all of the serum from the centrifuged tube, into a second tube.

However, in a preferred embodiment of the invention, there are a multiplicity of tubes, one within the other, with the inner tube being porous or open at its base, and the inner tube being easily withdrawable from the outer tube after centrifuging the outer tube (with inner tube therein), with inner and/or outer tubes of typically teflon(TM), slidable but snugly fitted within and flush against (preferably flush against) the inner walls of the outer tube, so as to result in substantially all of the blood sample remaining within the inner tube prior to subjecting the device to centrigugal action forces and to the thereafter withdrawal of the inner tube from the outer tube by which the coagulant precipitant within the inner tube becomes withdrawn from the outer tube, leaving the serum within the outer tube. In a further preferred embodiment, and as a part of a preferred use of this preferred device, after blood specimen is placed into the normally and preferably evacuated inner tube's space, the tube is as usual plugged with an appropriate stopper-plug, if not already plugged, the stopper-plug serving to firmly become wedged into the inner tube which securely but easily withdrawably becoming plugged-into the outer vessel, and after the plugging, the tube(s) is inverted for up-side-down subjection to centrifugal action forces thereof, with the result that the slidable material of intermediate specific gravity is located after centrifuging, with the blood solids coagulant precipitate thereby located at the upper end of the inner tube and adjacent the stopper-plug, wherein when the inner tube is withdrawn from the outer tube, the coagulant precipitate is withdrawn together with the withdrawal of the inner tube while the serum drains from the pores or open lower portion or base portion of the inner tube, into the outer tube base to remain within the outer tube which thereby is the container for thereafter solely the serum itself. The withdrawal of the inner tube (and the coagulant precipitate wedged therein by virtue of the intermediate specific gravity-material also wedged within the inner tube against the coagulant precipitate) is preferably effected as a result of dislodging the stopper-plug from the outer tube while the inner tube's mouth never-the-less remains wedged sealably and clingingly upon the terminal end of the stopper-plug.

Accordingly, after withdrawal of the blood specimen from the subject patient, the blood-containing tubes above-described, merely has to have the needle withdrawn from the stopper-plug and then inverted and placed for centrifuging thereof in the inverted state after which the plug is removed, preferably the plug upon removal also pulling with it — as described above — the inner tube concurrently, thereby avoiding the necessity of a separate subsequent operation of grasping and withdrawing the inner tube after the withdrawal of the stopper-plug. This leaves the outer tube with the serum therein, a very simple, non-expensive, and speedy procedure, while the elements of the combination are also very low cost and uncomplicated, these factors adding substantially to the utility of the invention in so far as the economics of the situation, as well as not requiring skill nor excessive time in the use of such device and procedure, as well as substantially eliminating any possibility of loss of suitability of a blood serum specimen even by an unskilled fast working and inexperienced technician.

THE FIGURES

FIG. 1 illustrates an exploded view of a typical preferred embodiment of the inventive device of the invention, in in-part view of the inner tubular vessel.

FIG. 2 illustrates the embodiment of FIG. 1 shown in a side cross-section view taken along the elongated longitudinal axis thereof.

FIG. 3 illustrates also in cross-section through the inner and withdrawn tube, the inner tube of the FIG. 1 embodiment with the clotted and centrifuged blood solids coagulant precipitate wedged within an upper portion of the inner tube by the embedded intermediate disk therebelow as would be the situation after the withdrawal of the inner tube and stopper-plug from the mouth of the outer tube subsequent to the inverted centrifuging thereof of the blood containing tube after initial coagulation of the contained blood specimen.

FIG. 4 illustrates a side cross-section view of the embodiments of FIGS. 1 and 2 together with the assembled conventional holder and inserted needle which needle is conventionally beveled at both ends thereof.

FIG. 5 illustrates a cross-sectional view as taken along lines 5—5 of FIG. 6, across a longitudinal axis of the disk and the inner tube, with the disk position at a preferred location at a lower end of the inner tube, and illustrating perforations within a concave lower face of the end of the disk for utility as shall be described hereinafter.

FIG. 6 illustrates a longitudinal sectional view as taken in cross-section along line 6-6 of FIG. 5 common embodiment of FIG. 5.

FIG. 7 illustrates an in-part view in side cross-sectional section through an alternate embodiment in which in a single tube the intermediate specific gravity-material as a gel composition is deposited adjacent an open end of the single tube in abutment with the stopper-plug, the needle outlet end being pierceable into and through each of the stopper-plug and gel composition to deposit blood specimen beneath the gel composition into the space therebelow, such that without inverting the tube, the tube may be centrifuged with itself in an upright state, whereby the gel composition of intermediate specific gravity wedges and packs the clotted coagulant precipitant into the bottom of the tube during the centrifuging of the blood specimen, whereby the serum would thereby be located between the stopper-plug and the gel composition and be easily pourable, or withdrawn by pipette or the like, or decanted into a second tube.

DETAILED DESCRIPTION

FIGS. 1 through 6 represent basically a common embodiment, except that in FIG. 6 the preferred lower positioning of the disk 14 is illustrated, whereby when the specimen is added into the interior space 22, most of the blood specimen will initially be above the disk 14, such that upon inversion before centrifugal action, most blood specimen will naturally and inherently remain within the space 22, rather than getting into the outer tube space 29 as might be the case in the positioning of disk 14 as shown in FIG. 4. The FIG. 6 also illustrates, however a feature common to all of FIGS. 1 through 5, namely the preferred concave lower face of the disk 14 such that when inverted, any blood specimen within the tube base space 29 of tube 12 tends to drain centrally of the concave face 24 into the perforations 25, this being particularly true in that the slidable tube 13 is flush with the inner tube sides of the outer tube 12; in each of the embodiments as represented by typically FIGS. 1 through 6, the chemical and physical properties of the respective inner and outer tubes are conventionally selected such that the inner tube, although flush with the inner surface of the outer tube, is easily slidable within the outer tube. The result is that the inner tube may be flushly in contact with the outer tube devoid of space therebetween but the inner tube easily inserted into and withdrawn from the outer tube, while the lack of space make it improbable that any blood specimen can get between the outer surface of the inner tube 13 and the inner surface of the outer tube 12, and also makes the drainage from the inner base walls of the outer tube 12 of specimen thereon ascertainable onto the concave surface 24 and through the pores or perforations 25 during the inversion and centrifugal action whereby none of the coagulated centrifuged coagulant precipitate ends up outside of the inner tube 13, whereby contamination of the serum eventually left within the outer tube is avoided.

Thus, the outer tube 12 and inner tube 13 and disk 14 and stopper-plug 15 make up the unitary device 7 shown in the exploded state in FIG. 1, in the combined state in FIGS. 2, 4, 5, & 6, and in FIG. 4 shown within the holder 9 with needle mount 10 and blood withdrawal-needle cover 11 and needle 30, as combination 8. The FIGS. 1-6 embodiment include outer tube 12 with its inner space 29, inner tube 13 with its inner space 22, outer tube 12 with its upper open mouth 26, and inner tube 13 with its lower open end 28 (which may be, if desired, merely perforations within a conventional tube) and upper mouth 27, and the disk 14 typically having guiding legs 17a, 17b, and 17c which are optional but preferred in order to prevent the disk 14 from becoming twisted and accidentally wedged within the inner space 22; however, a predetermined minimum length of the disk 14 will accomplish the same result. The stopper plug 15 is designed as a wedge preferably, as shown, but also preferably with slit 18 forming legs 19a and 19b, facilitating the wedging of the lower part of the stopper-plug securely into the upper mouth 27 of inner tube 13 such that the inner tube is inherently withdrawn upon removal of the stopper-plug from its plugging position and stage within the mouth 26 as shown in FIG. 2, the withdrawn state of the inner tube 12 being shown in FIG. 3. FIG. 4 illustrates basically the same embodiment as the FIGS. 1, 2, 3, 5, and 6, but does also illustrate a variation in that there is the insert 14a which is of a material through which blood cannot normally pass prior to forces thereon of a centrifugal nature, such that prior to inverting and prior to centrifuging in the inverted state, the blood remains trapped within the space 22 by virtue of the collapsed but extendable plastic drape 31 sealably anchored at points 32 (onto the tube 13) and 33 (onto the lower edge of disk 14a), and upon being centrifuged in the inverted state after placing the specimen into the space 22, the serum passes through the disk material of disk 14a into the space 29 while the coagulant precipitate remains within the space 22 and is moved by centrifugal forces toward the plug 15.

FIG. 3 further illustrates a state of being subsequent to centrifuging of a specimen in the inverted state and subsequent to the withdrawal of the stopper-plug 15 together with the still-attached inner tube 13 with the centrifuged coagulant precipitate 20a wedged between the stopper 15 and the disk 14, and between the stopper-plug legs 19a and 19b, and with a portion of the coagulant precipitate 20b possibly wedged beside the disk 14 extending possibly to a point 20c, as a result of the disk 14 having been moved in directions 21 within the space 22 during the action of the centrifugal forces thereon.

Typically the disk 14 preferably includes minor strengthening backing struts 23 as best seen in FIGS. 1, 5, and 6.

FIG. 7 illustrates another embodiment in which the material of intermediate specific gravity is of a suitable compactable material such as a conventional gel not readily soluble in water or in blood serum, and as in this particular embodiment is positioned within a sole tube at the mouth thereof such that the whole blood specimen may be placed beneath the material 14', whereby by placing the tube in the centrifuge in the normal upright position and state and centrifuging the same, the coagulated blood beneath the material 14' results in the serum being readily available for decanting thereof from the mouth of the tube while the centrifuged coagulant precipitate will be thereby packed into the bottom of the tube within space 29' segregated from the serum by virtue of the gel composition material 14' which will be packed on-top-of the coagulant precipitate, thereby enabling easy decanting of or otherwise conventional removal of the serum from the tube 12' after removal of the stopper-plug 15' subsequent to the centrifuging in the upright state.

It is within the scope and spirit of the present invention to make such variations and modifications and substitution of equivalents as would be obvious to a person skilled in this particular art.

I claim:

1. A blood serum-coagulant separation device comprising in combination:

a tubular vessel having a closed end and an open-mouth end thereof:

closure means for the open-mouth end of said tubular vessel, said closure means being penetrable by a tubular needle for introducing into the space within the separation device blood withdrawn from a subject;

a separation means for causing serum to become segregated from coagulant when the separation device is subjected to centrifugal forces after the filling or partial filling of the space within the tubular vessel with the withdrawn blood, said separation means being a substantially solid material having a specific gravity substantially greater than the specific gravity of blood serum and less than the specific gravity of the coagulant precipitate of blood; and a tubular container located within said tubular vessel, said tubular container having an outside diameter substantially the same as but slightly less than the inside diameter of said tubular vessel, said tubular container having two open ends, one end being adjacent to the open end of the tubular vessel and the other end, the base-opening end, being adjacent to the closed end of the tubular vessel, said separation means being located within said tubular container, said separation means having an outside diameter substantially the same as but slightly less than the inside diameter of the tubular container, and the said tubular container having a serum outlet opening in the lower portion thereof, whereby upon filling of interior space within the tubular container with blood, then centrifuging the assembly of tubular vessel and container invertedly mounted in the centrifuge, the serum, by virtue of its specific gravity, becomes located at the closed end of the tubular vessel and and thus located at the base-opening end of the tubular container, and the coagulant precipitate being thereby finally located in the tubular container at the end adjacent the mouth of the tubular vessel, whereby the tubular container may be removed from the tubular vessel thereby simultaneously removing the coagulant precipitate and thereby leaving solely serum within the tubular vessel.

2. A tubular vessel serum separation device of claim 1, in which the closure means seals open upper ends of each of the tubular vessel and tubular container when inserted thereinto.

* * * * *